(12) United States Patent
Moradi et al.

(10) Patent No.: US 9,890,120 B2
(45) Date of Patent: Feb. 13, 2018

(54) PREPARATION OF N-[(6-CHLOROPYRIDIN-3-YL)METHYL]-2,2-DIFLUOROETHAN-1-AMINE BY ALKYLATION OF 2,2-DIFLUOROETHYLAMINE

(71) Applicant: BAYER CROPSCIENCE AKTIENGESELLSCHAFT, Monheim am Rhein (DE)

(72) Inventors: Wahed Ahmed Moradi, Monheim (DE); Guenter Schlegel, Leverkusen (DE); Albert Schnatterer, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 1 day.

(21) Appl. No.: 15/126,593

(22) PCT Filed: Mar. 18, 2015

(86) PCT No.: PCT/EP2015/055639
§ 371 (c)(1),
(2) Date: Sep. 16, 2016

(87) PCT Pub. No.: WO2015/140198
PCT Pub. Date: Sep. 24, 2015

(65) Prior Publication Data
US 2017/0081284 A1     Mar. 23, 2017

(30) Foreign Application Priority Data
Mar. 21, 2014  (EP) ..................... 14161110

(51) Int. Cl.
*C07D 213/61* (2006.01)
*C07D 213/38* (2006.01)

(52) U.S. Cl.
CPC ......... *C07D 213/38* (2013.01); *C07D 213/61* (2013.01)

(58) Field of Classification Search
CPC .................. C07D 213/61; C07D 213/38
USPC ....................................... 546/329
See application file for complete search history.

(56) References Cited

U.S. PATENT DOCUMENTS

| 8,106,211 | B2 | 1/2012 | Jeschke et al. | |
| 8,273,897 | B2 | 9/2012 | Lui et al. | |
| 8,324,393 | B2 | 12/2012 | Lui et al. | |
| 8,404,855 | B2 | 3/2013 | Jeschke et al. | |
| 8,466,293 | B2 | 6/2013 | Lui et al. | |
| 8,546,577 | B2 | 10/2013 | Jeschke et al. | |
| 9,376,389 | B2 | 6/2016 | Funke et al. | |
| 2009/0253749 | A1* | 10/2009 | Jeschke | C07D 213/04 514/336 |
| 2010/0048646 | A1* | 2/2010 | Jeschke | A01N 47/40 514/357 |
| 2010/0204480 | A1* | 8/2010 | Lui | C07C 227/08 546/284.4 |
| 2010/0324103 | A1* | 12/2010 | Jeschke | A01N 43/40 514/357 |
| 2012/0123130 | A1* | 5/2012 | Lui | C07C 209/08 546/329 |
| 2015/0322011 | A1* | 11/2015 | Funke | C07D 213/61 546/329 |

FOREIGN PATENT DOCUMENTS

| WO | 2007/115644 A1 | 10/2007 |
| WO | 2009/036900 A1 | 3/2009 |
| WO | 2009/036901 A1 | 3/2009 |
| WO | 2011/157650 A1 | 12/2011 |
| WO | 2014/001245 A1 | 1/2014 |

OTHER PUBLICATIONS

Zhang; J. Med. Chem. 2002, 45, 2832-2840.*
Jia; Huagong Shikan (Chemical Industry Times), 2003, 17, 56-58, CAS records from CAPLUS and CASREACT databases, 2 pp.*
International Search Report dated May 8, 2015, issued in PCT/EP2015/055639.
European Search Report dated May 28, 2014, issued in counterpart application No. EP 14161110.

* cited by examiner

*Primary Examiner* — Daniel R Carcanague
(74) *Attorney, Agent, or Firm* — McBee Moore Woodward & Vanik IP, LLC

(57) ABSTRACT

A process for preparing N-[(6-chloropyridin-3-yl)methyl]-2,2-difluoroethan-1-amine of formula (III) wherein 2,2-difluoroethylamine of formula (I) is reacted with a halide of formula (II) in the presence of a hydroxide of an alkali metal or alkaline earth metal.

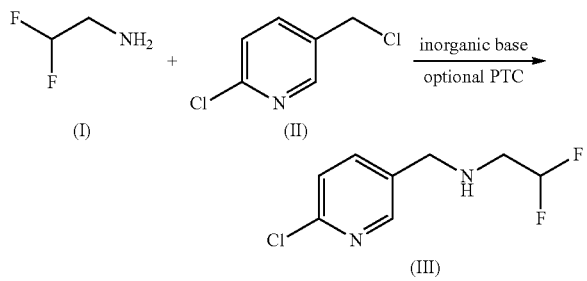

5 Claims, No Drawings

PREPARATION OF N-[(6-CHLOROPYRIDIN-3-YL)METHYL]-2,2-DIFLUOROETHAN-1-AMINE BY ALKYLATION OF 2,2-DIFLUOROETHYLAMINE

CROSS REFERENCE TO RELATED APPLICATIONS

This application is a § 371 National Stage Application of PCT/EP2015/055639, filed Mar. 18, 2015, which claims priority to EP 14161110.3, filed Mar. 21, 2014.

BACKGROUND

Field of Invention

The present invention relates to a novel economically and ecologically efficient process for preparing N-[(6-chloropyridin-3-yl)methyl]-2,2-difluoroethan-1-amine from 2,2-difluoroethylamine and 2-chloro-5-(chloromethyl)pyridine (CCMP) in the presence of an inorganic base, wherein the inorganic base is selected from the group consisting of alkali metal hydroxides and alkaline earth metal hydroxides.

Description of Related Art

N-[(6-Chloropyridin-3-yl)methyl]-2,2-difluoroethan-1-amine is an important intermediate in the preparation of agrochemical active ingredients (see WO-A-2007/115644). Various processes for preparing N-[(6-chloropyridin-3-yl)methyl]-2,2-difluoroethan-1-amine have been described. However, the existing processes have various disadvantages as described below.

For example, WO-A-2009/036900 discloses a process for preparing N-[(6-chloropyridin-3-yl)methyl]-2,2-difluoroethan-1-amine by amide hydrogenation of N-[(6-chloropyridin-3-yl)methyl]-2,2-difluoroacetamide (scheme 1).

Scheme 1:

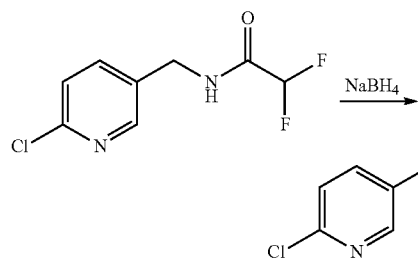

The disadvantage of this process is that it employs complex and very costly hydrides such as sodium borohydride which require highly elaborate safety measures.

WO 2009/036901 describes the reduction of N-(6-chloropyridin-3-yl)methylene-2,2-difluoroethanamine with hydrogen (scheme 2).

Scheme 2:

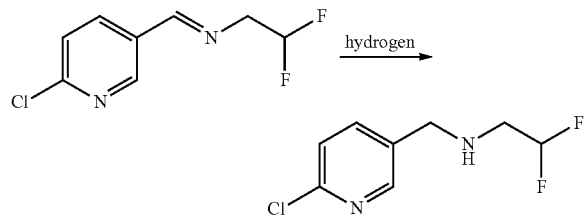

The disadvantage of this process is that it employs hydrogen, since here too the use of hydrogen requires highly elaborate safety measures.

WO-A-2011/157650 describes the preparation of 2,2-difluoroethanamine derivatives from 2,2-difluoro-1-haloethanes and primary amines in the presence of organic bases (scheme 3).

Scheme 3:

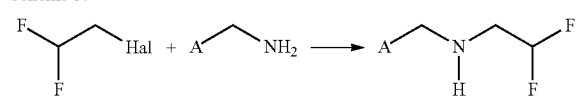

The disadvantage of this process is that the reaction needs to be carried out in a high-pressure apparatus.

Patent publication WO-A-2007/115644, concerning the preparation of insecticidally active 4-aminobut-2-enolide compounds, describes the preparation of compounds of general formula A—CH$_2$—NH—R$^1$, where A represents specific heterocycles and R$^1$ represents haloalkyl, by alkylation of the nitrogen (scheme 4).

Scheme 4:

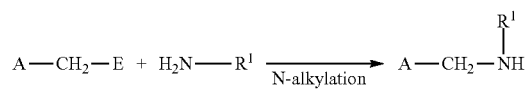

E=hal, for example chlorine, bromine, iodine; O-tosyl, O-mesyl,

Specifically, WO-A-2007/115644 describes the preparation of N-[(6-chloropyridin-3-yl)methyl]-2,2-difluoroethan-1-amine (compound (3)) which is synthesized from CCMP (compound (2)) and 2,2-difluoroethan-1-amine (compound 1)) in the presence of triethylamine (see scheme 5). Compounds (1), (2) and triethylamine are employed in equimolar amounts. The desired product is obtained in a yield of 53%.

Scheme 5:

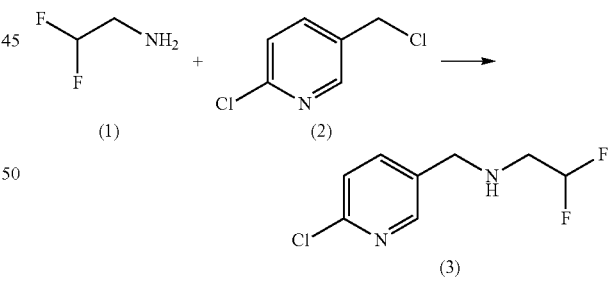

The process described in WO-A-2007/116544 for preparing compounds of formula A—CH$_2$—NH—R$^1$, where A represents specific heterocycles and R$^1$ represents haloalkyl, is disadvantageous since polyalkylation of the nitrogen may occur during the reaction. This leads to yield loss which is also apparent in the yield of the specifically cited example. The yield was only 53%. These polyalkylations can be reduced only by using a large excess of amine However, the distillative recovery of the costly amine is generally laborious and leads to losses.

WO-A-2014/001245 describes a process for preparing N-[(6-chloropyridin-3-yl)methyl]-2,2-difluoroethan-1- amine in the presence of N,N-diisopropylethylamine (Hünig's base). However, WO-A-2014/001245 does not disclose carrying out the reaction in the presence of an inorganic base such as NaOH for example.

Hünig's base is a very costly base which is difficult to obtain on a large industrial scale and which is employed in equimolar amounts in the process according to WO-A-2014/001245. Following the reaction, the base is present in the aqueous phase in the form of the amine hydrochloride. In order to recover the free base it is necessary to admix the aqueous phase with an inorganic base, separate the phases and subject the organic phase to a distillative work-up. The distillative recovery of the valuable Hünig's base is generally laborious and leads to losses. The aqueous phase moreover likewise comprises the Hünig's base, namely in typical concentrations of about 1 wt % as free Hünig's base. This leads to further losses. The free Hünig's base moreover contaminates the wastewater and the wastewater thus requires additional aftertreatment.

However, due to the significance of N-[(6-chloropyridin-3-yl)methyl]-2,2-difluoroethan-1-amine as a building block in the synthesis of agrochemical active ingredients it is necessary to find a process which can be employed economically and on a large industrial scale. It is also desirable to obtain N-[(6-chloropyridin-3-yl)methyl]-2,2-difluoroethan-1-amine in high yield and purity, so that the target compound preferably need not be subjected to any further—potentially complex—purification.

SUMMARY

A process for preparing N-[(6-chloropyridin-3-yl)methyl]-2,2-difluoroethan-1-amine has now been found which avoids the disadvantages of the existing processes, is moreover very simple, economic and environmentally friendly to carry out and may thus be employed on a large industrial scale. In particular, the novel process according to the invention eschews the use of Hünig's base.

The present invention thus relates to a process for preparing N-[(6-chloropyridin-3-yl)methyl]-2,2-difluoroethan-1-amine of formula (III)

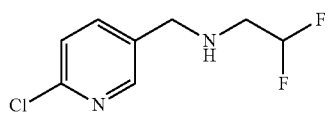

(III)

wherein 2,2-difluoroethylamine of formula (I)

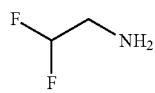

(I)

is reacted with 2-chloro-5-(chloromethyl)pyridine of formula (II)

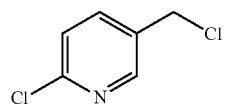

(II)

in the presence of an inorganic base, wherein the inorganic base is selected from the group consisting of alkali metal hydroxides and alkaline earth metal hydroxides.

The reaction according to the invention is shown in scheme 6.

Scheme 6:

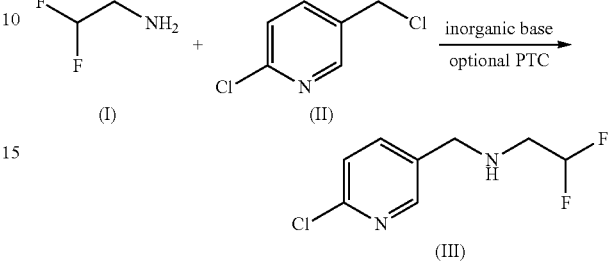

DETAILED DESCRIPTION OF A PREFERRED EMBODIMENT

The process according to the invention affords the desired N-[(6-chloropyridin-3-yl)methyl]-2,2-difluoroethan-1-amine of formula (III) in very good yields and high purity.

This is surprising since those skilled in the art could not assume that the employed 2,2-difluoroethylamine of formula (I) is stable in the presence of hydroxides of an alkali metal or alkaline earth metal as inorganic base (which are generally strong bases) such as NaOH or KOH. On the contrary, it was to be expected that the inorganic base would deprotonate the 2,2-difluoroethylamine of formula (I) at the fluorinated carbon atom to effect an elimination reaction and that the 2,2-difluoroethylamine derivative would then undergo polymerization, cyclization or some other reaction.

The process according to the invention affords the desired compound in a purity which generally renders unnecessary an extensive work-up of the reaction product. The process by-produces the chloride of the alkali metal or alkaline earth metal employed with the inorganic base, for example NaCl when NaOH is used as inorganic base. This is a great advantage over the processes described in WO-A-2014/001245 and WO-A-2007/115644.

The process according to the invention furthermore makes it possible to achieve using the economic inorganic base, yields which are comparable with or even higher than those achieved using the processes described in WO-A-2007/115644 and WO-A-2014/001245 wherein triethylamine (WO-A-2007/115644) and Hünig's base (WO-A-2014/001245) respectively are employed as tertiary nitrogen base. This is the case particularly when NaOH is used as inorganic base.

The process according to the invention is effected in the presence of an (i.e. precisely one or else more (e.g. two or three)) inorganic base selected from the group consisting of alkali metal hydroxides and alkaline earth metal hydroxides. Preferred inorganic bases are alkali metal hydroxides, in particular NaOH and KOH. Likewise preferred inorganic bases are Ca(OH)$_2$ and Mg(OH)$_2$.

The inorganic base is preferably employed neat or as an aqueous solution in the process according to the invention. The reaction mixture is thus preferably biphasic. Surprisingly, the inorganic base is effective despite the biphasicity of the reaction system.

Using the inorganic base in the process according to the invention has the advantage that practically all of the unconsumed 2,2-difluoroethylamine (I) may thus be distilled off easily and returned once more to the process as reactant. The process may thus be carried out in a manner which is particularly economic in terms of costs and resources.

Using NaOH makes it possible to achieve yields higher than those achieved using other inorganic bases. This is also apparent from the examples. It is thus very particularly preferable to employ NaOH in the process according to the invention.

The reaction of 2,2-difluoroethylamine with CCMP is exothermic and the reaction is thus preferably effected under relatively mild reaction temperatures for reasons of process safety.

It has been found that, surprisingly, in the further presence of a phase-transfer catalyst (PTC) the reaction can be carried out under relatively mild conditions. Accordingly, this alternative version of the process also forms part of the subject-matter of the invention.

In the process according to the invention, the molar ratio of the inorganic base (based on $OH^-$) to the employed CCMP of formula (II) is preferably in the range of from 10:1 to 0.1:1. It is more preferably in the range of from 5:1 to 0.5:1 and most preferably in the range of from 2:1 to 1:1. The use of larger quantities of inorganic base is possible in principle but generally uneconomic. The inorganic base may also be used in catalytic quantities.

In the process according to the invention, 2,2-difluoroethylamine of formula (I) is preferably used in excess. The molar ratio of CCMP of general formula (II) to the 2,2-difluoroethylamine employed is preferably in the range of from 1:1.5 to 1:20, more preferably in the range of from 1:2 to 1:10 and most preferably of from 1:2.5 to 1:5.

Since the reactants are liquid, the process according to the invention may be carried out without an additional reaction solvent. It will be appreciated that the reaction may also be carried out in the presence of a solvent.

The reaction according to the invention may be carried out over a wide temperature range (e.g. in the range of from 1° C. to 100° C.). The reaction is preferably carried out over a temperature range of from 30° C. to 60° C.

The reaction is preferably carried out at atmospheric pressure (i.e. 950-1050 mbar absolute). However, the process may in principle also be carried out at elevated pressure or reduced pressure.

The reaction time is short and is preferably in the range of from 0.5 to 5 hours. A longer reaction time is possible but generally economically unviable.

To work up the reaction mixture, the excess 2,2-difluoroethylamine (DFEA) employed is preferably distillatively recovered and may be reused.

Following the distillation of DFEA, the reaction mixture may optionally and preferably be admixed with an inert solvent—for example toluene, xylene, butyronitrile or n-butanol—and with water and the DFEA may subsequently be separated off.

Following optional pH adjustment of the solution, preferably to a value in the range of from 5.5-6, N-[(6-chloro-pyridin-3-yl)methyl]-2,2-difluoroethan-1-amine is separated off. The 2,2-difluoroethylamine derivative of formula (III) may subsequently be isolated at atmospheric pressure or under reduced pressure, preferably by distillation.

The inorganic base is preferably employed neat or as an aqueous solution. Accordingly, in one preferred embodiment the process according to the invention is carried out in the presence of water and in the further presence of a phase-transfer catalyst (PTC).

Phase-transfer catalysts (PTC) are in principle known to a person skilled in the art. It is preferable when precisely one phase-transfer catalyst is employed. However, it is also possible to employ two or yet more different phase-transfer catalysts. Particularly useful and preferably employed phase-transfer catalysts are organic ammonium or phosphonium salts, in particular tetraalkylammonium salts, benzyltrialkylammonium salts, tetraalkylphosphonium salts, benzyltrialkylphosphonium salts and mixtures thereof.

Among these, preference is given to organic ammonium salts, in particular tetraalkylammonium salts, benzyltrialkylammonium salts. Salts of this type include, for example, tetra-n-butylammonium chloride or bromide, tetra-n-butylammonium hydrogensulphate, tri-n-butylmethylammonium chloride or bromide, tri-n-butylmethylammonium hydrogensulphate, benzyltriethylammonium chloride or bromide, benzyltriethylammonium hydrogensulphate, trioctylmethylammonium chloride or bromide and trioctylmethylammonium hydrogensulphate.

Particular preference is given to using the commercially available tetra-n-butylammonium chloride or bromide and the commercially available trioctylmethylammonium chloride.

The phase-transfer catalyst is employed in catalytic quantities and those skilled in the art may select said phase-transfer catalyst and determine useful concentrations thereof by routine experiment.

It is nevertheless advantageous when the quantity of the phase-transfer catalyst employed is in the range of from 0.01 to 30 mol % based on the CCMP of formula (II). Said quantity is preferably in the range of from 0.05 to 5 mol %, more preferably in the range of from 0.1 to 3 mol %, based on the CCMP of formula (II).

Using a phase-transfer catalyst makes it possible to carry out the reaction under relatively mild reaction conditions. This may be a process safety requirement and also has the advantage of reduced secondary component formation. The reaction mixture can be worked up more easily which in turn may lead to higher yields of the desired target product.

Using a phase-transfer catalyst makes it possible to carry out the process under relatively mild reaction conditions and thus makes the process economically more advantageous.

In another preferred embodiment, the process is carried out in the absence of a phase-transfer catalyst. It is surprising that the process may also be carried out in the absence of a phase-transfer catalyst despite the biphasicity of the reaction system.

EXAMPLES

The present invention is more particularly described with reference to the examples which follow without being limited thereto.

A. Experimental Procedure

Example 7 (Experiment 7, Inventive)

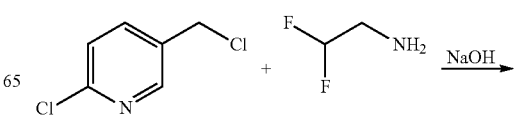

-continued

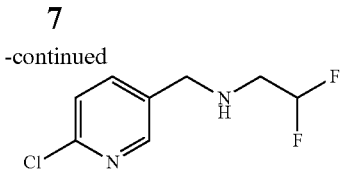

3684.7 g (45.0 mol) of 2,2-difluoroethylamine (DFEA, GC content: 99%) and 1931.1 g of NaOH (15.45 mol; 32%) are heated to 55° C. 496 g of a CCMP melt (CCMP, 3 mol, GC content: 98%) are added dropwise to this mixture over 0.5 hour at about 55° C. The reaction mixture is initially stirred for a further 2 hours at 55° C. A further 1983.9 g of CCMP (CCMP, 12 mol, 98%) are then added dropwise over 2 hours. The suspension is stirred for a further 2 hours at about 55° C. Excess DFEA is distilled off under reduced pressure at about 55° C. and between 325 and 120 mbar, 1968 g of butanol and 1750 g of water are added and the organic phase is separated off. This affords 5420.8 g of a solution of N-[(6-chloropyridin-3-yl)methyl]-2,2-difluoroethan-1-amine in n-butanol with a GC purity of 55.7 wt %. The chemical yield of N-[(6-chloropyridin-3-yl)methyl]-2,2-difluoroethan-1-amine determined by GC using an external standard and based on the CCMP employed is 97.40%.

Example 6 (Experiment 6, Inventive with TBAB)

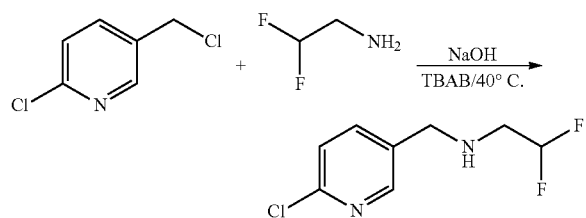

121.60 g (1.50 mol) of 2,2-difluoroethylamine (DFEA, GC content: 98%), 1.21 g of tetra-n-butylammonium bromide (TBAB, 3.75 mmol) and 64.37 g of NaOH (0.52 mol; 32%) are heated to 40° C. 16.29 g of CCMP (0.1 mol, GC content: 99.5%, distilled CCMP) are added dropwise to this mixture over 0.5 hour at about 40° C. The reaction mixture is initially stirred for a further 2 hours at 40° C. A further 65.16 g of CCMP (0.4 mol, GC content: 99.5%, distilled CCMP) are then added dropwise over 2 hours. The suspension is stirred for a further 2 hours at about 40° C. Excess DFEA is distilled off under reduced pressure at about 40° C., 89.8 g of butyronitrile and 75 g of water are added and the organic phase is separated off. This affords 212 g of a solution of N-[(6-chloropyridin-3-yl)methyl]-2,2-difluoroethan-1-amine in butyronitrile with a GC purity of 44.9%. The chemical yield of N-[(6-chloropyridin-3-yl)methyl]-2,2-difluoroethan-1-amine determined by GC using an external standard and based on the CCMP employed is 92.12%.

Only Example 6 was carried out under relatively mild conditions of 40° C., and the reaction was terminated before it had ended. The yields achieved are thus lower than in Examples 7-14 in which NaOH is likewise employed as inorganic base.

Examples 1-5, 8-15 and 17

All other examples carried out with and without TBAB and the corresponding base (Examples 1-5, 8-15 and 17) were carried out analogously to Example 7 and in the experiments with TBAB the initial reaction mixture comprised DFEA, the base and TBAB and was heated to 55° C.

Example 16 (According to WO-A-2007/115644) Using Triethylamine as Base

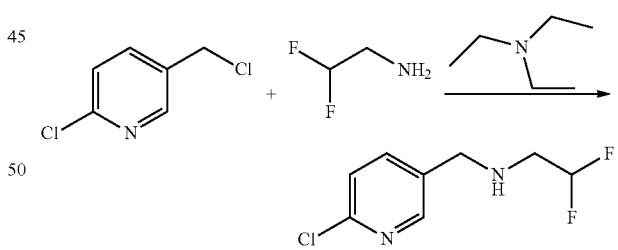

74.4 g (0.90 mol) of 2,2-difluoroethylamine (content: 98%) and 48.5 g (0.48 mol) of triethylamine (content: 99%) are heated to 55° C. 49.5 g (0.30 mol) of CCMP (content: 98%) are added dropwise to this mixture over 2.5 hours at this temperature. The yellow solution is stirred for a further 2 hours at this temperature and 74.0 g of a mixture of 2,2-difluoroethylamine and triethylamine are then distilled off.

According to GC using an external standard the recovery of excess 2,2-difluoroethylamine is 0.50 mol (83%) and the recovery of excess triethylamine is 0.11 mol (60%).

The residue is admixed with 217 g of toluene and 55 g of water, cooled down to 20° C. and 20% hydrochloric acid is added to set a pH of 6. The bottom aqueous phase is separated off and the solvent is distillatively removed from the organic phase.

The chemical yield of N-[(6-chloropyridin-3-yl)methyl]-2,2-difluoroethan-1-amine determined by HPLC using an external standard and based on the CCMP employed is 62%.

Example 17 Using Triethylamine as Base (Non-Inventive)

86.0 g (1.05 mol) of 2,2-difluoroethylamine (DFEA, GC content: 99%) and 36.85 g of triethylamine (0.36 mol; 99%) are heated to 55° C. 11.57 g of a CCMP melt (CCMP, 0.07 mol, GC content: of a CCMP melt (CCMP, 3 mol, GC content: 98%) are added dropwise to this mixture over 0.5 hour at about 55° C. The reaction mixture is initially stirred for a further 2 hours at 55° C. A further 46.29 g of CCMP (CCMP, 0.28 mol, 98%) are then added dropwise over 2 hours. The suspension is stirred for a further 2 hours at about 55° C. Excess DFEA is distilled off under reduced pressure at about 55° C. and between 325 and 120 mbar, butanol and water are added and the organic phase is separated off. This affords 211 g of a solution of N-[(6-chloropyridin-3-yl)

methyl]-2,2-difluoroethan-1-amine in n-butanol with a GC purity of 27.94 wt %. The chemical yield of N-[(6-chloropyridin-3-yl)methyl]-2,2-difluoroethan-1-amine determined by GC using an external standard and based on the CCMP employed is 81.87%.

B. Results:

(Experiments 1, 2, 3, 5, 15, 16 and 17 are Non-Inventive, Experiments 4 and 6-14 are Inventive)

TABLE 1

| Experiment | Base | Phase-transfer catalyst [mol %] | Solvent | Extractant | Yield [std. GC %] |
|---|---|---|---|---|---|
| 1 | Hünig's base | none | n-PrCN | n-PrCN | 92.9 |
| 2 | none | none | 4 eq. DFEA | none | 88.7 |
| 3 | Na₂CO₃ | none | water/DFEA | n-PrCN | 72.4 |
| 4 | KOH | 3 mol % of TBAB | none | n-butanol | 84.5 |
| 5 | Na₂CO₃ | 3 mol % of TBAB | none | n-butanol | 82.5 |
| 6 ⁴⁰° ᶜ· | NaOH | 0.75 mol % of TBAB | none | n-PrCN | 93.1 |
| 7 | NaOH | none | none | n-butanol | 97.4 |
| 8 | NaOH | none | n-PrCN | n-PrCN | 98.4 |
| 9 | NaOH | none | xylene | xylene | 97.2 |
| 10 | NaOH | 2 mol % of TBAB | none | n-butanol | 96.7 |
| 11 | NaOH | 1 mol % of TBAB | none | n-butanol | 96.0 |
| 12 | NaOH | 0.5 mol % of TBAB | none | n-butanol | 95.2 |
| 13 | NaOH | 0.5 mol % of TBAB | none | n-butanol | 95.2 |
| 14 | NaOH | 0.75 mol % of TBAB | none | n-PrCN | 98.8 |
| 15 | Na₂CO₃ | none | water/DFEA | n-PrCN | 72.4 |

TBAB: tetra-n-butylammonium bromide (phase-transfer catalyst).
Hünig's base: N,N-diisopropylethylamine (base from WO-A-2014/001245).
n-PrCN: butyronitrile.
KOH (85 wt %)
DFEA: 2,2-difluoroethylamine.
eq.: equivalents.

The results (experiments 1-17) show that
- the reaction may be carried out with good yields using inorganic bases which makes it possible to simultaneously avoid all of the disadvantages associated with using Hünig's base (difficult to obtain on a large industrial scale, laborious work-up and recovery etc.),
- the reaction may be carried out using inorganic bases to achieve yields distinctly higher than those achieved using triethylamine as base (Examples 16 and 17 according to WO-A-2007/115644),
- using hydroxides of an alkali metal (NaOH, KOH) as inorganic base made it possible to achieve yields distinctly higher than those achieved using other inorganic bases (Na₂CO₃). The yields achieved using NaOH or KOH as inorganic base were between 84.5% and 98.8% (Examples 4, 6-14) while the yields achieved using Na₂CO₃ as inorganic base were only in the region of 72.4% and 82.5% (Examples 3, 5 and 15).
- the highest yields were achieved using NaOH as inorganic base (93.1%-98.8%),
- the reaction is succcessful both in the presence and in the absence of a phase-transfer catalyst (TBAB).

The invention claimed is:

1. Process for preparing N-[(6-chloropyridin-3-yl)methyl]-2,2-difluoroethan-1-amine of formula (III)

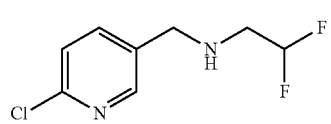

(III)

wherein 2,2-difluoroethylamine of formula (I)

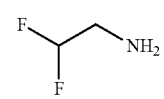

(I)

is reacted with 2-chloro-5-(chloromethyl)pyridine of formula (II)

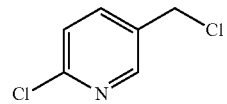

(II)

in the presence of an inorganic base, wherein the inorganic base is NaOH.

2. Process according to claim 1, wherein the reaction is carried out in the presence of a phase-transfer catalyst.

3. Process according to claim 2, wherein the phase-transfer catalyst is an organic ammonium or phosphonium salt.

4. Process according to claim 1, wherein the reaction is carried out in the absence of a phase-transfer catalyst.

5. Process according to claim 1, wherein the unconsumed 2,2-difluoroethylamine of formula (I) is distilled off following the reaction and subsequently returned to the process as reactant.

* * * * *